United States Patent
Zhang et al.

(10) Patent No.: US 11,096,978 B2
(45) Date of Patent: Aug. 24, 2021

(54) COMMON BEAN (PHASEOLUS VULGARIS) EXTRACT WITH HIGH A-AMYLASE INHIBITORY ACTIVITY AND LOW HEMAGGLUTININ ACTIVITY

(71) Applicant: Mellitas Health Foods, LLC, Ithaca, NY (US)

(72) Inventors: Sha Zhang, Ithaca, NY (US); Zhong Zhang, Ithaca, NY (US)

(73) Assignee: MELLITAS HEALTH FOODS, LLC, Ithaca, NY (US)

(*) Notice: Subject to any disclaimer, the term of this patent is extended or adjusted under 35 U.S.C. 154(b) by 73 days.

(21) Appl. No.: 16/155,291

(22) Filed: Oct. 9, 2018

(65) Prior Publication Data

US 2019/0216874 A1 Jul. 18, 2019

Related U.S. Application Data

(60) Provisional application No. 62/616,508, filed on Jan. 12, 2018.

(51) Int. Cl.
*A61K 36/48* (2006.01)

(52) U.S. Cl.
CPC .......... *A61K 36/48* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 7,354,606 B2 | 4/2008 | Murray et al. | |
| 7,579,027 B2 | 8/2009 | Birketvedt | |
| 9,290,752 B2 | 3/2016 | Sarama et al. | |
| 9,868,581 B2 | 1/2018 | Gorman et al. | |
| 2009/0042779 A1 | 2/2009 | Boilini et al. | |
| 2009/0093397 A1 | 4/2009 | Berlanda et al. | |
| 2014/0273157 A1 | 9/2014 | Sarama et al. | |

OTHER PUBLICATIONS

Koaze et al, Part I. Isolation of two Kinds of Acid-proteases Excreted by Aspergillus niger var. macrosporus, 1964, Agr. Biol. Chem., 28: 216-223.*
PCT International Search Report and Written Opinion for PCT/US2019/013300, dated Apr. 29, 2019.
Kotaru, M. et al., "Activity changes in cranberry bean (Phaseolus vulgaris) alpha-amylase inhibitor by chemical modification and enzymatic digestion", Journal of Nutritional Science and Vitaminology, 1969, vol. 35, No. 1, pp. 71-80.
Liener, I. E., "Inactivation studies on the soybean hemagglutinin", Journal of Biological Chemistry, 1958, vol. 233, No. 2, pp. 401-405.

* cited by examiner

*Primary Examiner* — Terry A McKelvey
*Assistant Examiner* — Catheryne Chen
(74) *Attorney, Agent, or Firm* — Kevin E. West; Advent, LLP

(57) ABSTRACT

An improved method for making a *P. vulgaris* bean extract that results in an extract having high α-amylase inhibitory activity and low hemagglutinin activity. The method involves treating the beans to selectively denature the hemagglutinin. A *P. vulgaris* bean extract is provided, having high α-amylase inhibitory activity and low hemagglutinin activity. A treatment for diabetes or method for reducing blood glucose level is disclosed using the *P. vulgaris* bean extract disclosed herein.

11 Claims, 2 Drawing Sheets

| Example | Conditions | α-Amylase inhibitory activity (%) | Hemagglutinin activity (HAU/g) |
|---|---|---|---|
| 1a | Control- No enzymes; no pH 3 treatment | 92.7 | 5,120,000 |
| 1b | Control- No enzymes; no pH 3 treatment | 94.6 | 5,818,181 |
| 2a | Fungal acid protease (0.24g) and papain (0.09g); pH 3; 1 hour | 84.7 | 6,400 |
| 2b | Fungal acid protease (0.24g); pH 3; 1 hour | 84.4 | 51,000 |
| 2c | Fungal acid protease (0.2g) and papain (0.1g); pH 3; 2 hours | 74.5 | 114 |
| 2d | Fungal acid protease (0.3g) and papain (0.14g); pH 3; 1 hour | 81.7 | 114 |
| 3 | Commercial bean extract | 10.3 | 111,636 |
| 4 | No enzymes; pH 3 | 73.7% | 315,076 |

FIG. 2

COMMON BEAN (PHASEOLUS VULGARIS) EXTRACT WITH HIGH A-AMYLASE INHIBITORY ACTIVITY AND LOW HEMAGGLUTININ ACTIVITY

CROSS REFERENCE TO RELATED APPLICATION

This application claims priority to U.S. Provisional Application Ser. No. 62/616,508, filed on Jan. 12, 2018.

BACKGROUND

*Phaseolus vulgaris* is a bean species also known as the common bean. Certain *P. vulgaris* varieties, such as white kidney beans, contain a glycoprotein, α-amylase inhibitor, which has been shown to inhibit the activity of pancreatic α-amylase in mammals. White bean extract (phaseolamin) has been marketed for weight loss for humans, for example, because of this ability to inhibit the activity of human pancreatic α-amylase and thus prevent dietary starch converting to simple sugars. Purified white bean extract has been shown to reduce the blood glucose level in human and animal subjects.

White beans also contain lectins, called phytohemagglutinins or hemagglutinins due to their ability to agglutinate human red blood cells. Eating soaked raw or uncooked white beans can cause food poisoning due to the large amount of hemagglutinin in raw white beans. Therefore, before consuming white beans, the beans must be treated to remove or denature the hemagglutinin. Generally, for consumption purposes, the beans are cooked to denature the hemagglutinin.

Since both α-amylase inhibitor and hemagglutinins are proteins, when the beans are heat treated to denature the hemagglutinins, the α-amylase inhibitor is also denatured and its inhibitory activity on α-amylase is greatly diminished. Therefore, there is a need for methods of making *P. vulgaris* bean extract wherein the hemagglutinin is removed or denatured but the α-amylase inhibitory activity is not substantially reduced.

SUMMARY

This summary is provided solely as an introduction to subject matter that is fully described in the detailed description and drawings. The summary should not be considered to describe essential features nor be used to determine the scope of the claims. Moreover, it is to be understood that both the summary and the detailed description are examples and explanatory only and are not necessarily restrictive of the subject matter claimed.

An improved method for making a *P. vulgaris* extract is disclosed which results in an extract having high α-amylase inhibitory activity and low hemagglutinin activity. The method preferably involves soaking the beans and extracting the proteins. The protein extract is treated by a method which selectively denature the hemagglutinin without substantially affecting the α-amylase inhibitory activity. The method for treating the protein extract comprises a low pH treatment, an enzymatic treatment, or a combination.

In one embodiment, the *P. vulgaris* extract is made from the bean known as the white kidney bean (cannellini bean). In other embodiments the extract is made from one or more *P. vulgaris* varieties such as the white kidney bean and other white beans, including navy beans, great northern beans, lima beans, and red kidney beans.

In another embodiment, a *P. vulgaris* bean extract is provided, having high α-amylase inhibitory activity and low hemagglutinin activity.

In another embodiment, a treatment for diabetes or method for reducing blood glucose level is disclosed using the *P. vulgaris* bean extract disclosed herein.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 2 is a table illustrating the α-amylase inhibitory activity and hemagglutinin activity for example extracts.

DETAILED DESCRIPTION

Figure 1:
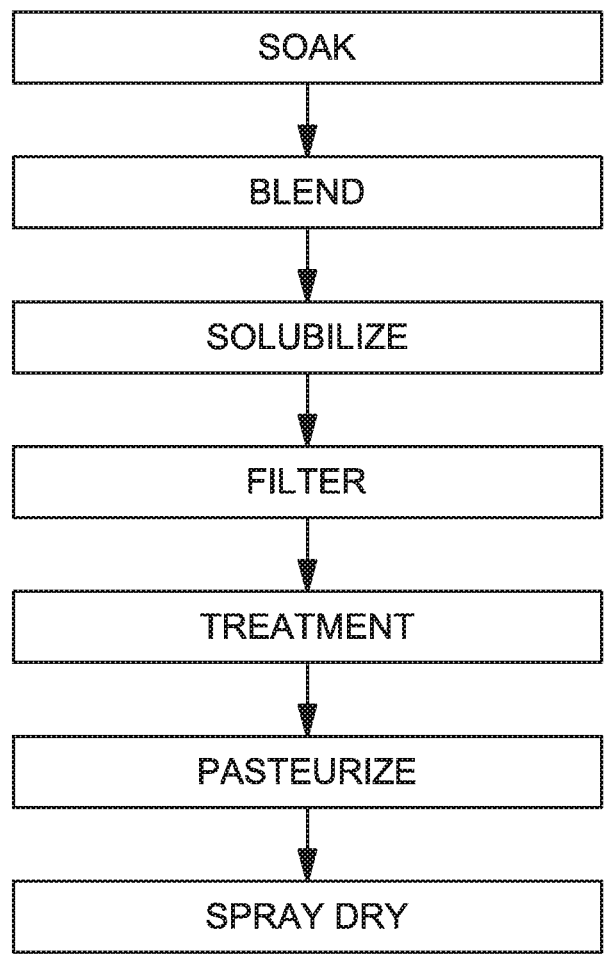
FIG. 1 is a flow chart showing one embodiment of a method of the present disclosure.

As shown in FIG. 1, the method of making the *P. vulgaris* extract has several steps, some of which may be omitted, altered, or conducted in an alternate order than herein described. The steps as described here perform functions that may be accomplished using another technique. In addition, additional treatment or purification steps can be performed, and/or additional steps to formulate the final extract product.

In a first step for solubilization of the proteins, as shown in FIG. 1, the *P. vulgaris* beans may be soaked in an aqueous solution. Water can be used, for example, or a buffer having a pH that does not denature the α-amylase such as from about pH 5 to 9, desirably about pH 6 to 8. The length of this soak can be from about 1 to 100 hours, generally an overnight soak is sufficient, from about 5 to 20 hours. The primary purpose is to break down the structure of the beans so that the enzymatic treatments are more effective.

The soaked beans may be further broken down using a blender, for example, or another method to break down the beans into a suspension of bean starches and bean proteins. As the bean proteins are released from the bean they will be solubilized into the aqueous phase after some time of exposure to the aqueous solution. In a next step, the aqueous protein containing solution may be treated, such as by filtration or centrifugation to remove insoluble material. The resulting solution contains the α-amylase inhibitor and the hemagglutinins.

To denature the hemagglutinins in the separated bean solution, a treatment is used which substantially denatures the hemagglutinins but does not substantially diminish the α-amylase inhibitory activity of the extract. In one aspect, this treatment is an enzymatic treatment with a single enzyme or a combination of enzymes. Generally, an effective amount of one or more enzymes is added to the filtered aqueous solution and allowed to act on the hemagglutinin therein. It may be desirable to adjust the pH of the solution before or after the enzymes are added, since generally each enzyme functions better at a certain pH. For example, an acidic pH of about 2 to 4 may be beneficial. The solution can be heated for more effective and faster enzymatic action. This may include heating to a temperature of between about 40° C. and 70° C., preferably between about 50° C. to 60° C., most preferably about 55° C. for about 1 to 4 or even 1 to 2 hours.

Enzymes which can be used include, but are not limited to, one or more of fungal acid protease, papain, bromelain, fungal protease, dipeptidyl aminopeptidase, bacterial protease, trypsin, or pepsin. The best conditions for the enzymatic treatment may be selected based on the enzyme(s) used.

The one or more enzymes are added in an amount effective to achieve denaturation of the hemagglutinin. This can be about 0.005% to 1.0% compared to filtered extract, on a weight basis.

In another aspect, the treatment to substantially denature the hemagglutinins but which does not substantially diminish the α-amylase inhibitory activity of the extract is a low pH treatment. The pH of the filtered aqueous solution is adjusted to an acidic pH of about 2 to 4. The solution can be heated for more effective and faster action. This may include heating to a temperature of between about 40° C. and 70° C., preferably between about 50° C. to 60° C., for about 1 to 4 or even 1 to 2 hours.

A pasteurization step can be applied after enzymatic and/or pH treatment, involving heating the extract at effective amount of time. Generally, a temperature from about 60 to 85° C. is beneficial, more desirably about 65 to 75° C. or about 70° C. and generally 0.5 to 30 minutes, about 10 to 20 minutes, or about 15 minutes is effective.

If desired, the extract may be spray dried into a powder as a final product. Alternatively, or in addition, the product may be freeze dried.

A *P. vulgaris* bean extract prepared according to the above method desirably inhibits between about 70% to 100% of α-amylase activity in a porcine pancreatic amylase assay, desirably between about 80% to 100%, or between about 80% to 100% of the α-amylase activity. Moreover, a *P. vulgaris* bean extract prepared according to the above method desirably has hemagglutinating activity units per gram below 400,000, preferably below about 100,000 or below about 60,000 hemagglutinating activity units per gram.

The disclosure includes a method for treating diabetes or for reducing blood glucose level comprising administering an effective dose of the *P. vulgaris* bean extract described herein. The invention also includes a method of promoting weight loss comprising administering an effective dose of the *P. vulgaris* bean extract described herein.

An effective dose can be determined by methods known to those skilled in the art. For example, an effective dose might be determined to be a dose effective to block the breakdown of a quantity of starch in a typical meal, for example about 60 to 100 grams of starch.

The extract may be further formulated for administration, such as by formulation with a suitable carrier. The extracts may be formulated into various forms such as tablets, capsules, liquids, etc. In one embodiment, the extracts may be formulated into food products, such as drinks or solid supplements.

EXAMPLES

The examples below serve to further illustrate the present disclosure, to provide those of ordinary skill in the art with a complete disclosure and description of how the compounds, compositions, articles, devices, and/or methods claimed herein are made and evaluated, and are not intended to limit the scope of the present disclosure. In the examples, unless expressly stated otherwise, amounts and percentages are by weight, temperature is in degrees Celsius or is at ambient temperature, and pressure is at or near atmospheric. The examples are not intended to restrict the scope of the present disclosure.

Example 1—Control

The control was conducted in duplicate (Examples 1a and 1b). 200 g of white kidney beans were soaked in 1600 g of water overnight. Then the soaked beans were blended by a blender for about 10 mins. The blended mixture was kept at room temperature for about 4 hours with occasionally stirring to extract the bean proteins into the water phase. The mixture was then filtered through a few layers of cheese cloth to remove most of the insoluble matter. The volume of the filtered extract was about 1350 mL.

270 g of the filtered extract was removed and the temperature of the extract was brought to about 70° C. for 15 minutes for pasteurization. After pasteurization, the extract was cooled using a cold-water bath and stored in a refrigerator. The extract was spray dried into powder form using a bench-top spray dryer.

α-Amylase activity.

The amylase inhibitory activity was tested using porcine pancreatic amylase (Sigma-Aldrich A6255). The amylase concentration was 22 μL in 50 mL buffer. The spray dried extracts were rehydrated into water solution at a ratio of 1 g of sample to 19 g of phosphate buffer solution (PBS). In the test, 22 μL of porcine pancreatic amylase was diluted into 50 mL of PBS buffer (pH 6.9). Soluble starch in PBS solution was used in the amylase inhibition test. Reducing sugar was tested by dinitrosalicylic colorimetric method.

Hemagglutinin activity.

The hemagglutinin denaturation was measured using trypsinized rabbit red blood cells. Hemagglutinin activity is reported as hemagglutinating unit per gram (HAU/g).

Example 2a—Fungal Acid Protease and Papain 270 g of the filtered extract from Example 1 was removed and the pH of the filtered extract was adjusted to 3.0 using 20% (w/w) citric acid solution. The pH adjusted filtered extract was placed into a water bath with a pre-set temperature of 59° C. and stirred for 1 hour.

When the temperature of the pH adjusted filter extract reached 54° C., 0.24 g of fungal acid protease and 0.09 g of papain were added and the treated extract sat while stirring for 1 hour. The extract was cooled to room temperature by placing the container into cold water. The pH of the extract was adjusted to 6.40 using sodium hydroxide solution. Then the temperature of the extract was brought to about 70° C. for 15 minutes for pasteurization. After pasteurization, the extract was cooled using a cold-water bath and stored in a refrigerator. The extract was spray dried into powder form using a bench-top spray dryer.

Example 2b—Fungal Acid Protease

Another 270 g portion of filtered bean extract was removed and subjected to the same procedure as Example 2a except fungal acid protease alone was used instead of the fungal acid protease/papain combination.

Example 2c—Second Sample of Fungal Acid Protease and Papain

The same method as above was used except that 200 g filtered bean extract was used, to which 0.20 g of fungal acid protease and 0.10 g of papain were added. In addition, the enzyme treatment lasted for 2 hours.

Example 2d—Third Sample of Fungal Acid Protease and Papain

The same method as above was used except that 200 g filtered bean extract was used, to which 0.30 g of fungal acid protease and 0.14 g of papain were added; the enzyme treatment was for 1 hour.

Examples 1 and 2 Results

The results are shown in FIG. 2. Control samples without enzymatic treatment (Examples 1a and 1b) inhibited 92.7% (94.6%) of the amylase activity and exhibited hemagglutinin activity of 5,120,000 HAU/g (5,818,181 HAU/g). Example 2a (fungal acid protease and papain) inhibited 84.7% of the amylase activity and had 6,400 HAU/g. Example 2b (only fungal acid protease) inhibited 86.4% of the amylase activity and hemagglutinin activity of 51,000 HAU/g.

Example 2c inhibited 74.48% of the amylase activity. Example 2d inhibited 81.7% of the amylase activity. The hemagglutinating unit per gram (HAU/g) of both samples 2c and 2d was 114 HAU/g.

Compared to control, the enzymatic method of the present disclosure significantly reduced the hemagglutinin activity levels in the bean extract while not substantially affecting its amylase inhibitory activity.

Example 3—Commercial Bean Extract

A commercial bean extract was assayed for α-amylase inhibition and hemagglutinating activity and only had 10.3% α-amylase inhibition and more than 111,636 HAU/g of hemagglutinating activity.

Example 4—pH Treatment, No Enzyme 100 g of white kidney beans were soaked in 700 g of water overnight. Then the soaked beans were blended by a blender for about 10 mins. The mixture was then filtered through a few layers of cheese cloth to remove most of the insoluble matters.

200 g of the filtered extract was removed and the pH of the filtered extract was adjusted to pH 3.0 using 20% (w/w) hydrochloric acid. The filtered extract at pH 3.0 was placed into a water bath with pre-set temperature of 59° C. and stirred for 1 hour. The extract was cooled to room temperature by placing the stainless container into cold water. The pH of the extract was adjusted to 6.4 using sodium hydroxide solution. Then the temperature of the extract was brought to about 70° C. for 15 minutes for pasteurization. After pasteurization, the extract was cooled by cold water and stored in a refrigerator.

Hemagglutinin activity measured 315,076 HAU/g, significantly lower than the controls but higher than the samples treated with enzymes. α-amylase inhibition was 73.7%.

Although the technology has been described with reference to the embodiments illustrated in the attached drawing figures, equivalents may be employed, and substitutions made herein without departing from the scope of the technology as recited in the claims. Modifications and variations of the present disclosure will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method for making a *P. vulgaris* bean extract having α-amylase inhibitory activity which inhibits between about 70% to 100% of the α-amylase activity and hemagglutinin activity per gram (HAU/g) below 400,000 comprising the step of subjecting the *P. vulgaris* beans to a treatment that denatures hemagglutinin so that the HAU/g is reduced by at least 99.0% but does not substantially reduce α-amylase inhibitory activity; wherein the treatment is a combination of pH treatment of between 2-4 and enzymatic treatment and wherein the enzymatic treatment comprises using one or more enzymes selected from the group fungal acid protease, papain, bromelain, fungal protease, dipeptidyl aminopeptidase, bacterial protease, trypsin, and pepsin.

2. The method of claim 1, wherein the *P. vulgaris* bean is selected from the varieties white kidney beans, cannelloni beans, navy beans, great northern beans, and red kidney beans.

3. The method of claim 1, comprising the steps:
   i) solubilizing *P. vulgaris* bean proteins including hemagglutinin and α-amylase inhibitor into an aqueous solution; and
   ii) contacting the protein containing solution with one or more enzymes which denature hemagglutinin so that the HAU/g is reduced by at least 99.0% but do not substantially affect the inhibiting activity of α-amylase inhibitor.

4. The method of claim 3, wherein the step of solubilization includes soaking the *P. vulgaris* beans in an aqueous solution and breaking down the soaked *P. vulgaris* beans into a suspension including bean proteins.

5. The method of claim 3, wherein the enzymatic treatment step is conducted at a pH between about 2 to about 4 and a temperature of between about 40° C. and 70° C.

6. The method of claim 4, further comprising the step of pasteurizing the enzymatically treated solution.

7. The method of claim 6, further comprising the step of spray drying the pasteurized solution.

8. The method of claim 1, comprising the steps:
   i) solubilizing *P. vulgaris* bean proteins including hemagglutinin and α-amylase inhibitor into an aqueous solution; and
   ii) reducing the pH of the protein containing solution to a pH between 2 and 4 for a time sufficient to denature hemagglutinin so that the HAU/g is reduced by at least 99.0%.

9. The method of claim 1 wherein the method results in an extract which inhibits between about 80% to 100% of the α-amylase activity.

10. The method of claim 1, wherein the method results in an extract which has hemagglutinating activity units per gram below about 100,000.

11. The method of claim 1, wherein the method results in an extract which has hemagglutinating activity units per gram below about 60,000.

* * * * *